US006426060B2

(12) United States Patent
Franklin et al.

(10) Patent No.: US 6,426,060 B2
(45) Date of Patent: *Jul. 30, 2002

(54) COSMETIC COMPOSITIONS

(75) Inventors: Kevin Ronald Franklin; Andrew Hopkinson, both of Bebington (GB)

(73) Assignee: Unilever Home & Personal Care USA a division of Conopco, Inc., Chicago, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/548,309

(22) Filed: Apr. 12, 2000

(30) Foreign Application Priority Data

Apr. 12, 1999 (GB) ............................................. 9908212

(51) Int. Cl.⁷ ................................................. A61K 7/32
(52) U.S. Cl. ........................... 424/65; 424/401; 424/66; 424/68
(58) Field of Search ................................ 424/401, 865, 424/66, 68

(56) References Cited

U.S. PATENT DOCUMENTS

| 5,635,165 | A | | 6/1997 | Panitch | 424/65 |
| 5,849,276 | A | | 12/1998 | Guskey et al. | 424/65 |
| 6,086,887 | A | * | 7/2000 | Parrott | 424/195.1 |

FOREIGN PATENT DOCUMENTS

| EP | 0736545 | 10/1996 |
| WO | 97/16163 | 5/1997 |

OTHER PUBLICATIONS

Communication Relating to Results of Partial International Search—Application No. PCT/GB 00/01235.
JP 60/076543 to Takashi et al. (5/85) assigned to Kobayashi Kose KK, (Derwent Abstract).
Nobuhiro et al. "Gelation of Fully Acylated Cellobiose in Alkane Solution", Bull. Chem. Soc. Jpn, vol. 168, 1995, pp. 3423–3428, XP–002127501.
Takada et al. "Discotic Collunmar Liquid Crystals in Oligosaccharide Derivatives III. Anomeric Effects on the Thermo–Mesomorphic Properties of Cellobiose Octa–Alkanoates"—Liquid Crystals, vol. 19, No. 4, 1995, pp. 441–448—XP–000545756.

* cited by examiner

Primary Examiner—Jose' G. Dees
Assistant Examiner—Konata M. George
(74) Attorney, Agent, or Firm—Kevin J. Stein

(57) ABSTRACT

A cosmetic composition is a structured emulsion of a continuous phase containing water-immiscible liquid carrier plus a structurant, and a disperse phase which is a solution of antiperspirant active in a more polar, probably aqueous, solvent. The structurant is a material which forms a network of fibers in the continuous phase, thereby gelling it. The structurant has an enthalpy of gelation in the carrier liquid or a test liquid with a magnitude of at least 30 kJ/mole. This minimum enthalpy of gelation facilitates processing at conveniently accessible temperatures and promotes stability.

29 Claims, No Drawings

COSMETIC COMPOSITIONS

FIELD OF THE INVENTION

The present invention relates to cosmetic compositions for application to human skin. Significant forms of the invention are concerned with antiperspirant compositions for application to human skin, especially the axilla. However, the invention can also be applied to other forms of cosmetic composition.

BACKGROUND OF THE INVENTION AND SUMMARY OF PRIOR ART

A wide variety of cosmetic compositions for application to human skin make use of a thickened or structured liquid carrier to deliver colour or some other active material to the surface of the skin. A significant example of such cosmetic compositions are antiperspirant compositions which are widely used in order to enable their users to avoid or minimise wet patches on their skin, especially in axillary regions.

Cosmetic compositions have been made in a variety of product forms. One of these is a so-called "stick" which is usually a bar of an apparently firm solid material held within a dispensing container and which retains its structural integrity and shape whilst being applied. When a portion of the stick is drawn across the skin surface a film of the stick composition is transferred to the skin surface. Although the stick has the appearance of a solid article capable of retaining its own shape for a period of time, the material usually has a structured liquid phase so that a film of the composition is readily transferred from the stick to another surface upon contact. Examples of cosmetic compositions which are, or can be, marketed in a stick form are lipsticks, lip salves and eyebrow pencils. The stick form has been used in particular for deodorant and antiperspirant compositions where the composition includes a deodorant active material or an antiperspirant active material respectively.

Another possibility is that a stick is a softer solid composition accommodated in a dispensing container which in use extrudes the composition through one or more apertures.

Antiperspirant sticks and other cosmetic compositions can be divided into three categories. Suspension sticks contain a particulate material, notably a particulate antiperspirant active material, suspended in a structured carrier liquid phase. Emulsion sticks normally have a hydrophilic phase forming an emulsion with a second, more hydrophobic, liquid phase. One of the phases contains an active material. Solution sticks typically have the active material dissolved in a structured liquid phase; this phase may be organic solvent or may be a mixture of water and a water-miscible organic solvent. This classification into suspension, emulsion and solution types can be applied to both firm and soft solid compositions.

Besides firm and soft sticks, a number of cosmetic compositions have taken the form of liquids which are formulated to be somewhat viscous and hence pour and flow more slowly than water. One example is antiperspirant compositions in liquid form, such as applied using a roll-on applicator.

There is substantial literature on the structuring or thickening of cosmetic compositions which is frequently accomplished using some form of thickening agent as part of the composition.

Some compositions have a substantial viscosity, which may even make them capable of retaining their own shape for a time, because of transient interactions between molecules of a thickening agent in the liquid.

This is characteristic of compositions which are thickened with polymers. Thickening can be attributed to interactions between polymer molecules.

It is characteristic of such thickened compositions that their viscosity can be achieved or recovered on standing at room temperature. If subjected to shear their viscosity reduces (hence they are described as shear thinning) but the viscosity recovers towards its original value if the composition is subsequently allowed to stand at room temperature.

Compositions which have two phases, such as emulsions may also have substantial viscosity, even to the extent of being able to sustain their own shape.

Here too it is characteristic of the composition that—provided the composition is stable—its viscosity will recover spontaneously if it is reduced by subjecting the composition to shear.

Compositions have also been given structure and an enhanced viscosity or rigidity by the incorporation of a structurant (also referred to as a gellant or gelling agent) which causes the liquid to gel upon cooling from an elevated temperature.

Gel formation takes place as an exothermic event within a temperature range referred to as the gel point or gel temperature. Upon reheating, melting of the gel takes place as an endothermic event within a temperature range. When the gel melts, the structurant goes into solution in the liquid. Such gels can be disrupted by shearing and do not recover their viscosity for a long time, if at all unless remelted, although a small partial recovery may be observed.

U.S. Pat. Nos. 4,265,878, 4,725,431, 4,719,103 and 4,704,271 disclose antiperspirant stick compositions in which a solution of antiperspirant active in aqueous solution is dispersed in a hydrophobic continuous phase of hydrocarbon or silicone oil. This hydrophobic continuous phase is structured to provide a rigid stick by the incorporation of a substantial amount of waxy material, such as stearyl alcohol or spermaceti wax. one material which is well known to form gels is 12-hydroxy stearic acid which is discussed in Terech et al "Organogels and Aerogels of Racemic and Chiral 12-hydroxy Octadecanoic Acid", Langmuir Vol 10, 3406–3418, 1994. The material is commercially available from Ajinomoto and from Caschem.

U.S. Pat. No. 5,750,096 is one of several documents which teaches that gelation of antiperspirant suspensions can be brought about using esters or amides of 12-hydroxy stearic acid. The alcohol used to form such an ester or the amine used to form such an amide may contain an aliphatic, cycloaliphatic or aromatic group with up to 22 carbons therein. If the group is aliphatic it preferably contains at least three carbon atoms. A cycloaliphatic group preferably contains at least five carbon atoms and may be a fixed ring system such as adamantyl.

WO 98/27954, WO 97/11678 and WO 98/34588 are examples of other documents disclosing the gelation of solutions and suspensions.

N-acyl amino acid amides and esters are also known to structure liquids. We have established that they do so by forming fibrous networks. They are described in U.S. Pat. No. 3,969,087. N-Lauroyl-L-glutamic acid di-n-butylamide is commercially available from Ajinomoto under their designation GP-1.

SUMMARY OF THE INVENTION

We have recognised that when a gel is formed, the solution of the structurant in a liquid may supercool before gelling commences, and in consequence the gel-melting temperature may be higher than the gel-formation temperature. If gel-formation takes place in a quiescent solution of the structurant the extent of supercooling may be substantial. We have observed that it varies from one structurant to another.

However, if the structurant is being used to prepare a product where a constituent such as a disperse phase is mixed into the hot liquid before gel formation, we have found that it is likely to be necessary to carry out this mixing operation at a temperature at which the structurant is fully soluble in the liquid. If an attempt is made to mix the composition at a temperature at which there is some supercooling, it is likely that the mixing will induce gelation to commence.

It is a consequence of this that when preparing structured liquid compositions containing a structurant to gel the liquid, all constituents of the composition must be subjected to a temperature high enough to dissolve the structuring agent.

We have now found that advantageous properties and processing can be provided in a cosmetic composition which is a structured emulsion, by utilising a gelling agent, in particular a gelling agent of moderate molecular weight, which has an enthalpy of gelation of at least 30 kilojoule per mole.

According to a first aspect of this invention there is provided a cosmetic composition which is a structured emulsion comprising:

i a continuous phase containing water-immiscible liquid carrier and a fibre-forming structurant present in the continuous phase, which is effective to gel the composition upon cooling from a temperature at which the structurant is in solution in the carrier liquid, and ii a disperse phase which is a solution of antiperspirant active in water, water-soluble solvent or a mixture of them, characterised in that the structurant has an enthalpy of gelation in the carrier liquid with a magnitude of at least 30 kJ/mole, preferably at least 35 kJ/mole, and more preferably at least 45kJ/mole, 48 kJ/mole or 50 kJ/mole.

The enthalpy of gelation can be determined by differential scanning calorimetry (DSC).

A gelling agent giving an enthalpy of gelation in this range of at least 30 or 35 kJ/mole upwards can give the advantage of allowing processing without requiring the entire composition to be subjected to high temperature. This can be valuable in preparing a composition which is an emulsion with a hydrophilic (e.g. aqueous) disperse phase. A further advantage resides in stability of the resulting gel. These advantages are more apparent if the enthalpy of gelation is higher (45 kJ per mole or more).

By contrast, if the enthalpy of gelation is low, one or both of two disadvantages are observed. Rather high processing temperatures may be needed and/or a gel may be formed but then undergo unwanted progressive transformation during storage, such as crystals appearing and growing, softening of the composition or leakage of liquid from it.

Although the enthalpy of gelation is a property of the structurant and carrier liquid jointly, we have found that it is predominantly a property of the structurant. Consequently, the measurement of enthalpy of gelation in one or several representative liquids is valuable as technique (which can be carried out with a small sample and a standard instrument) to assess the suitability of a potential structurant. It may be desirable to take a measurement in any one of several representative liquids, since some structurants do not gel all hydrophobic carrier liquids.

Therefore in a second aspect this invention provides a cosmetic composition which is a structured emulsion comprising i) a continuous phase containing water-immiscible liquid carrier and a fibre-forming structurant present in the continuous phase, which is effective to gel the composition upon cooling from a temperature at which the structurant is in solution in the carrier liquid, and ii) a disperse phase which is a solution of antiperspirant active in water, water-soluble solvent or a mixture of them characterised in that the structurant is able to gel one or more of decamethyl cyclopentasiloxane an 80:20 wt % mixture of decamethyl cyclopenta-siloxane and isostearyl alcohol isostearyl alcohol with an enthalpy of gelation in at least one of the liquids with a magnitude of at least 30 kJ/mole, preferably at least 35 kJ/mole, more preferably at least 45, 48 or 50 kJ/mole.

A composition according to this invention may take the form of a firm gel with apparent rigidity, or a soft solid which is able to retain its own shape for a time (for example if it is taken out of a mould without being subjected to shear) but which is easily deformed by hand pressure. Preferred within this invention are compositions which have sufficient rigidity that they can be regarded as firm solids. The hardness of such compositions can be measured with a penetrometer, in a manner which will be described in greater detail below.

Certain preferred forms of this invention are concerned with compositions which are translucent or transparent. As is already known, translucent or transparent compositions can be obtained if it is possible to match the refractive indices of the different constituent phases present in the composition.

We have found that compositions within this invention which are a novel transparent or translucent emulsion can be obtained by formulating the composition to meet two criteria. Firstly the disperse phase and the continuous phase (consisting of the water-immiscible carrier liquid and the structurant contained within that liquid)should be formulated so that their refractive indices match. The refractive index of the continuous phase will be close to the refractive index of the water-immiscible carrier liquid in it. In order to achieve good light transmission through a composition, the refractive index of the water-immiscible continuous phase and the refractive index of the disperse phase should match within 0.003 units preferably 0.002 units.

Secondly, the matched refractive indices of these two phases should lie in a range which is an approximate match to the refractive index of the structurant. The closeness of match required will depend on the structurant which is used. The refractive index of a structurant can be determined by making trial compositions as explained in more detail below. Such investigation will also show how closely the refractive index of the liquid must be matched to the structurant.

A composition of this invention will generally be marketed in a container by means of which it can be applied at time of use. This container may be of conventional type.

Another aspect of the invention therefore provides a cosmetic product comprising a dispensing container having at least one aperture for delivery of the contents of the container, means for urging the contents of the container to the said aperture or apertures, and a composition of either of the previous aspects of the invention in the container. Preferred is that a composition of this invention is sufficiently rigid to be accommodated as a stick product in a dispensing container having an open end at which an end portion of the stick of composition is exposed for use.

The compositions of this invention can be produced by processes in which the composition is produced as a mobile liquid at an elevated temperature and allowed to cool to permit gel-formation.

Thus, according to a further aspect of the present invention there is provided a process for the production of a cosmetic composition according to the first or second aspect of this invention comprising, not necessarily in any order, the steps of incorporating a structurant into a water-immiscible liquid carrier mixing the liquid carrier with a disperse liquid phase, heating the liquid carrier or a mixture containing it to an elevated temperature at which the structurant is soluble in the water-immiscible liquid carrier, suitably followed by introducing the mixture into a mould which preferably is a dispensing container, and then cooling or permitting the mixture to cool to a temperature at which it is thickened or solidified.

In this invention it is possible and indeed preferred that the step of mixing with a disperse phase, and any subsequent steps, are carried out at a temperature not exceeding 90° C. and possibly not exceeding 85° C.

It may be possible to keep below these temperatures throughout the process.

According to a yet further aspect of the present invention, there is provided a method for preventing or reducing perspiration on human skin comprising topically applying to the skin a composition as set forth earlier comprising an antiperspirant active in solution in the disperse phase of the composition, a water-immiscible liquid carrier and a structurant therefor.

DETAILED DESCRIPTION AND PREFERRED EMBODIMENTS

Measurement of enthalpy of gelation can be carried out using a small sample and standard DSC techniques.

Measurement should be carried out at a slow cooling rate and to promote consistency in measurement, it should, if possible, be carried out with the concentration in a standardised range or approximating to a standard value.

We have preferred to carry out measurement at a concentration of structurant in the liquid which is not over 8% by weight, preferably from 3%, better 6%, up to 8% by weight. Results at such concentrations are generally a close approximation to results at a standardised concentration of 7.5% by weight.

For any structurant which cannot dissolve at such a concentration, an alternative standardised concentration would be 3% by weight.

A gel may first be made by heating and cooling, and a sample of gel sealed in a calorimeter capsule. Alternatively the appropriate weights of liquid and structurant could be sealed in a calorimeter capsule, heated and allowed to cool to a gel in the capsule.

In a preferred procedure a gel is prepared containing from 7 to 7.5% by weight of structuring agent. Approximately 20 mg of the gel (for example between 18 and 22 mg) is weighed into a calorimeter capsule and sealed. It is then heated at 10 K/minute to a temperature at which the structuring agent is known to be fully soluble in the liquid, held for one minute at this temperature and then a DSC scan is taken while cooling at 2 K/minute.

The scan is repeated with a capsule containing approximately 20 mg of decamethyl cyclopentadisiloxane and in accordance with normal DSC technique, data collected with the liquid alone (multiplied by a scaling factor if necessary) is subtracted from the data collected with the gel, so that the gel-formation exotherm appears as a departure from a flat baseline. The enthalpy is the area between the peak and the baseline.

We have found it appropriate to carry out measurements, both on the gel and on the liquid alone, over a broad range of temperatures, such as from −50° C. to +150° C. for the sake of accuracy in subtracting one measurement from the other.

For calculation it is assumed that the exotherm (heat given out during gel formation) comes from the whole quantity of structuring agent present.

Structurant

A number of organic compounds are known to possess the ability to gel hydrophobic organic liquids such as water-immiscible hydrocarbon and/or silicone oils by formation of a network of fibres or strands which extends throughout the liquid, thereby gelling the liquid. Such materials are generally non-polymeric, being monomers or dimers with molecular weight below 10,000 rather than polymers with more than 8 repeat units or with molecular weight above 10,000.

Materials with this property have been reviewed by Terech and Weiss in "Low Molecular Mass Gelators of Organic Liquids and the Properties of their Gels" Chem. Rev 97, 3133–3159 [1997] and by Terech in Chapter 8, "Low-molecular weight Organogelators" of the book "Specialist surfactants" edited by I D Robb, Blackie Academic Professional, 1997.

It is characteristic of such structurants that they are able to gel the organic liquid in the absence of any disperse phase the structured liquids are obtainable by cooling from an elevated temperature at which the structurant is in solution in the liquid—this solution being mobile and pourable the structured liquid becomes more mobile if subjected to shear or stress the structure does not spontaneously recover within 24 hours if the sheared liquid is left to stand at room temperature even though a small partial recovery may be observed the structure can be recovered by reheating to a temperature at which the structurant is in solution in the liquid, and allowing it to cool back to room temperature.

It appears that such structurants operate by interactions which are permanent unless disrupted by shear or heating. Such structurants operate by forming a network of strands or fibres extending throughout the gelled liquid. In some cases these fibres can be observed by electron microscopy, although in other cases the observation of the fibres which are believed to be present is prevented by practical difficulties in preparing a suitable specimen. When observed, the fibres in a gel are generally thin (diameter less than $0.5\mu$, often less than $0.2\mu$) and appear to have numerous branches or interconnections.

From our observations made using differential scanning calorimetry we believe that fibrous networks consist of crystalline material. The crystalline fibres may or may not be the same polymorph as macroscopic crystals obtained by conventional crystallization from a solvent.

A novel structurant which is the subject of a co-pending application and which may be used in this invention is an ester of cellobiose and a fatty acid, preferably of 6 to 13 carbon atoms especially 8 to 11 carbon atoms. Preferably the cellobiose is fully esterified, or nearly so, and is in the α-anomeric form.

The structure of such a compound in its a-anomeric form is:

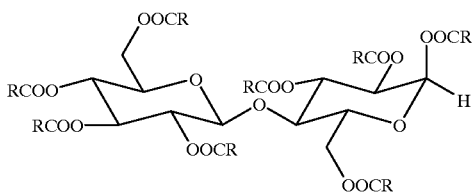

where R is an alkyl or alkenyl chain of 5 to 12 carbon atoms so that the acyl group contains 6 to 13 carbon atoms. Particularly preferred acyl groups incorporate a linear alkyl chain of 7 to 10 carbon atoms and are thus octanoyl, nonanoyl, decanoyl or undecanoyl.

The acyl groups may have a mixture of chain lengths but it is preferred that they are similar in size and structure. Thus it is preferred that all of the acyl groups are aliphatic and at least 90% of the acyl groups have a chain length within a range such that the shorter and longer chain lengths in the range differ by no more than two carbon atoms, i.e. length in a range from m−1 to m+1 carbon atoms where the mean acyl chain length m has a value in a range from 7 to 10 or 11. Commercially available feedstocks for these acyl groups are likely to include a small percentage of acyl groups which differ from the majority and may have a branched rather than linear chain. Thus it is likely that more than 90% but less than 100% of the acyl groups will meet the desired criterion of chain lengths in a range from m−1 to m+1 carbon atoms.

Linear aliphatic acyl groups may be obtained from natural sources, in which case the number of carbon atoms in the acyl group is likely to be an even number or may be derived synthetically from petroleum as the raw material in which case both odd and even numbered chain lengths are available.

Synthetic methods for the esterification of saccharides are well known. The esterification of cellobiose has been reported by Takada et al in *Liquid Crystals,* (1995) Volume 19, pages 441–448. This article gives a procedure for the production of the alpha anomers of cellobiose octa-alkanoates by esterification of β-cellobiose using an alkanoic acid together with trifluoracetic anhydride.

For this invention the structurant mnay be an esterified saccharide as discussed above but selected so that it also satisfies the criterion of an enthalpy of gelation of at least 30, preferably at least 45, kilojoule per mole.

Carrier Liquid

The water-immiscible carrier liquid in the continuous phase comprises one or a mixture of materials which are relatively hydrophobic so as to be immiscible in water. Some hydrophilic liquid may be included in the carrier, provided the overall carrier liquid mixture is immiscible with water. It will generally be desired that this carrier is liquid (in the absence of structurant) at temperatures of 15° C. and above. It may have some volatility but its vapour pressure will generally be less than 4 kPa (30 mmHg) at 25° C. so that the material can be referred to as an oil or mixture of oils. More specifically, it is desirable that at least 80% by weight of the hydrophobic carrier liquid should consist of materials with a vapour pressure not over this value of 4 kPa at 25° C.

It is preferred that the hydrophobic carrier material includes a volatile liquid silicone, i.e. liquid polyorganosiloxane. To class as "volatile" such material should have a measurable vapour pressure at 20 or 25° C. Typically the vapour pressure of a volatile silicone lies in a range from 1 or 10 Pa up to 2 kPa at 25° C.

It is desirable to include volatile silicone because it gives a "drier" feel to the applied film after the composition is applied to skin.

Volatile polyorganosiloxanes can be linear or cyclic or mixtures thereof. Preferred cyclic siloxanes include polydimethsiloxanes and particularly those containing from 3 to 9 silicon atoms and preferably not more than 7 silicon atoms and most preferably from 4 to 6 silicon atoms, otherwise often referred to as cyclomethicones. Preferred linear siloxanes include polydimethylsiloxanes containing from 3 to 9 silicon atoms. The volatile siloxanes normally by themselves exhibit viscosities of below $10^{-5}$ m$^2$/sec (10 centistokes), and particularly above $10^{-7}$ m$^2$/sec (0.1 centistokes), the linear siloxanes normally exhibiting a viscosity of below $5\times10^{-6}$ m$^2$/sec (5 centistokes). The volatile silicones can also comprise branched linear or cyclic siloxanes such as the aforementioned linear or cyclic siloxanes substituted by one or more pendant —O—Si(CH$_3$)$_3$ groups. Examples of commercially available silicone oils include oils having grade designations 344, 345, 244, 245 and 246 from Dow Corning Corporation; Silicone 7207 and Silicone 7158 from Union Carbide Corporation; and SF1202 from General Electric.

The hydrophobic carrier employed in compositions herein can alternatively or additionally comprise non-volatile silicone oils, which include polyalkyl siloxanes, polyalkylaryl siloxanes and polyethersiloxane copolymers. These can suitably be selected from dimethicone and dimethicone copolyols. Commercially available non-volatile silicone oils include Dow Corning 556 and Dow Corning 200 series.

The water-immiscible liquid carrier may contain from 0 to 100% by weight of one or more liquid silicones. Preferably, there is sufficient liquid silicone to provide at least 10%, better at least 15%, by weight of the whole composition. If silicone oil is used, volatile silicone preferably lies in a range from 20% possibly from 30 or 40% up to 100% of the weight of the water-immiscible carrier liquid. In many instances, when a non-volatile silicone oil is present, its weight ratio to volatile silicone oil is chosen in the range of from 1:3 to 1:40.

Silicon-free hydrophobic liquids can be used instead of, or more preferably in addition to liquid silicones. Silicon-free hydrophobic organic liquids which can be incorporated include liquid aliphatic hydrocarbons such as mineral oils or hydrogenated polyisobutene, often selected to exhibit a low viscosity. Further examples of liquid hydrocarbons are polydecene and paraffins and isoparaffins of at least 10 carbon atoms.

Other hydrophobic carriers are liquid aliphatic or aromatic esters.

Suitable aliphatic esters contain at least one long chain alkyl group, such as esters derived from $C_1$ to $C_{20}$ alkanols esterified with a $C_8$ to $C_{22}$ alkanoic acid or $C_6$ to $C_{10}$ alkanedioic acid. The alkanol and acid moieties or mixtures thereof are preferably selected such that they each have a melting point of below 20° C. These esters include isopropyl myristate, lauryl myristate, isopropyl palmitate, diisopropyl sebacate and diisopropyl adipate.

Suitable liquid aromatic esters, preferably having a melting point of below 20° C., include fatty alkyl benzoates. Examples of such esters include suitable $C_8$ to $C_{18}$ alkyl benzoates or mixtures thereof.

Further instances of suitable hydrophobic carriers comprise liquid aliphatic ethers derived from at least one fatty alcohol, such as myristyl ether derivatives e.g. PPG-3 myristyl ether or lower alkyl ethers of polyglycols such as PPG-14 butyl ether.

Aliphatic alcohols which are solid at 20° C., such as stearyl alcohol are preferably absent or present in low concentration such as less than 5% by weight of the whole composition since these lead to visible white deposits when a composition is used.

However, aliphatic alcohols which are liquid at 20° C. may be employed. These include branched chain alcohols of at least 10 carbon atoms such as isostearyl alcohol and octyl dodecanol.

Very polar materials are preferably excluded or present in only small quantity in the water-immiscible carrier liquid. Preferably therefore, this liquid or mixture of liquids contains not more than 10% of its own weight, better not more than 5%, of any constituent which is a water-miscible compound.

Silicon-free liquids can constitute from 0–100% of the water-immiscible liquid carrier, but it is preferred that silicone oil is present and that the amount of silicon-free constituents preferably constitutes up to 50 or 60% and in many instances from 10 or 15% up to 50 or 60% by weight of the carrier liquid.

If any oxygen-containing silicon-free organic liquids are included in the hydrophobic carrier liquid, the amount of them is likely to be not over 70% by weight of the carrier liquid. Smaller amounts, ranging up to 20, 30 or 35% by weight are likely.

The carrier liquid must be compatible with the structurant. If the structurant is too soluble or conversely is very insoluble in the carrier liquid it may fail to form a gel and the carrier liquid should be modified to alter its polarity.

Liquid Disperse Phase

A composition of this invention is an emulsion which contains a polar disperse phase. The disperse phase may be a solution of an active ingredient.

The hydrophilic disperse phase in an emulsion normally comprises water as solvent and can comprise one or more water soluble or water miscible liquids in addition to or replacement for water. The proportion of water in an emulsion according to the present invention is often selected in the range of up to 60%, and particularly from 10% up to 40% or 50% of the whole formulation.

One class of water soluble or water-miscible liquids comprises short chain monohydric alcohols, e.g. $C_1$ to $C_4$ and especially ethanol or isopropanol, which can impart a deodorising capability to the formulation. A further class of hydrophilic liquids comprises diols or polyols preferably having a melting point of below 40° C., or which are water miscible. Examples of water-soluble or water-miscible liquids with at least one free hydroxy group include ethylene glycol, 1,2-propylene glycol, 1,3-butylene glycol, hexylene glycol, diethylene glycol, dipropylene glycol, 2-ethoxyethanol, diethylene glycol monomethylether, triethyleneglycol monomethylether and sorbitol. Especially preferred are propylene glycol and glycerol.

In an emulsion the disperse phase is likely to constitute from 5 to 80 or 85% of the weight of the composition preferably from 5 to 50 or 65% more preferably from 25 or 35% up to 50 or 65%, while the continuous phase with the structurant therein provides the balance from 15 or 35% up to 95% of the weight of the composition. Compositions with a high proportion of disperse phase i.e. from 65 to 85% disperse phase may be advantageous because the large proportion of disperse phase can make a contribution to hardness.

An emulsion composition will generally include one or more emulsifying surfactants which may be anionic, cationic, zwitterionic and/or nonionic surfactants. The proportion of emulsifier in the composition is often selected in the range up to 10% by weight and in many instances from 0.1 or 0.25 up to 5% by weight of the composition. Most preferred is an amount from 0.1 or 0.25 up to 3% by weight. Nonionic emulsifiers are frequently classified by HLB value. It is desirable to use an emulsifier or a mixture of emulsifiers with an overall HLB value in a range from 2 to 10 preferably from 3 to 8.

It may be convenient to use a combination of two or more emulsifiers which have different HLB values above and below the desired value. By employing the two emulsifiers together in appropriate ratio, it is readily feasible to attain a weighted average HLB value that promotes the formation of an emulsion.

Many suitable emulsifiers of high HLB are nonionic ester or ether emulsifiers comprising a polyoxyalkylene moiety, especially a polyoxyethylene moiety, often containing from about 2 to 80, and especially 5 to 60 oxyethylene units, and/or contain a polyhydroxy compound such as glycerol or sorbitol or other alditol as hydrophilic moiety. The hydrophilic moiety can contain polyoxypropylene. The emulsifiers additionally contain a hydrophobic alkyl, alkenyl or aralkyl moiety, normally containing from about 8 to 50 carbons and particularly from 10 to 30 carbons. The hydrophobic moiety can be either linear or branched and is often saturated, though it can be unsaturated, and is optionally fluorinated. The hydrophobic moiety can comprise a mixture of chain lengths, for example those deriving from tallow, lard, palm oil, sunflower seed oil or soya bean oil. Such nonionic surfactants can also be derived from a polyhydroxy compound such as glycerol or sorbitol or other alditols. Examples of emulsifiers include ceteareth-10 to -25, ceteth-10–25, steareth-10–25 (i.e. C16 to C18 alcohols ethoxylated with 10 to 25 ethylene oxide residues) and PEG-15–25 stearate or distearate. Other suitable examples include $C_{10}$–$C_{20}$ fatty acid mono, di or tri-glycerides. Further examples include $C_{18}$–$C_{22}$ fatty alcohol ethers of polyethylene oxides (8 to 12 EO).

Examples of emulsifiers, which typically have a low HLB value, often a value from 2 to 6 are fatty acid mono or possibly diesters of polyhydric alcohols such as glycerol, sorbitol, erythritol or trimethylolpropane. The fatty acyl moiety is often from $C_{14}$ to $C_{22}$ and is saturated in many instances, including cetyl, stearyl, arachidyl and behenyl. Examples include monoglycerides of palmitic or stearic acid, sorbitol mono or diesters of myristic, palmitic or stearic acid, and trimethylolpropane monoesters of stearic acid.

A particularly desirable class of emulsifiers comprises dimethicone copolymers, namely polyoxyalkylene modified dimethylpolysiloxanes. The polyoxyalkylene group is often a polyoxyethylene (POE) or polyoxypropylene (POP) or a copolymer of POE and POP. The copolymers often terminate in $C_1$ to $C_{12}$ alkyl groups.

Suitable emulsifiers and co-emulsifiers are widely available under many trade names and designations including Abil™, Arlacel™, Brij™, Cremophor™, Dehydrol™, Dehymuls™, Emerest™, Lameform™, Pluronic™, Prisorine™, Quest PGPR™, Span™, Tween™, SF1228, DC3225C and Q2-5200.

Antiperspirant Actives

Antiperspirant actives, are preferably incorporated in an amount of from 0.5–60%, particularly from 5 to 30% or 40% and especially from 5 or 10% to 30 or 35% of the weight of the whole composition.

Antiperspirant actives for use herein are often selected from astringent active salts, including in particular aluminium, zirconium and mixed aluminium/zirconium salts, including both inorganic salts, salts with organic anions and complexes. Preferred astringent salts include aluminium, zirconium and aluminium/zirconium halides and halohydrate salts, such as chlorohydrates.

Aluminium halohydrates are usually defined by the general formula $Al_2(OH)_xQ_y.wH_2O$ in which Q represents chlorine, bromine or iodine, x is variable from 2 to 5 and x+y=6 while $wH_2O$ represents a variable amount of hydration. Especially effective aluminium halohydrate salts, known as activated aluminium chlorohydrates, are described in EP-A-6739 (Unilever NV et al), the contents of which specification is incorporated herein by reference. Some activated salts do not retain their enhanced activity in the presence of water but are useful in substantially anhydrous formulations, i.e. formulations which do not contain a distinct aqueous phase.

Zirconium actives can usually be represented by the empirical general formula: $ZrO(OH)_{2n-nz}B_z.wH_2O$ in which z is a variable in the range of from 0.9 to 2.0 so that the value 2n-nz is zero or positive, n is the valency of B, and B is selected from the group consisting of chloride, other halide, sulphamate, sulphate and mixtures thereof. Possible hydration to a variable extent is represented by wH20. Preferable is that B represents chloride and the variable z lies in the range from 1.5 to 1.87. In practice, such zirconium salts are usually not employed by themselves, but as a component of a combined aluminium and zirconium-based antiperspirant.

The above aluminium and zirconium salts may have coordinated and/or bound water in various quantities and/or may be present as polymeric species, mixtures or complexes. In particular, zirconium hydroxy salts often represent a range of salts having various amounts of the hydroxy group. Zirconium aluminium chlorohydrate may be particularly preferred.

Antiperspirant complexes based on the above-mentioned astringent aluminium and/or zirconium salts can be employed. The complex often employs a compound with a carboxylate group, and advantageously this is an amino acid. Examples of suitable amino acids include dl-tryptophan, dl-β-phenylalanine, dl-valine, dl-methionine and β-alanine, and preferably glycine which has the formula $CH_2(NH_2)COOH$.

It is highly desirable to employ complexes of a combination of aluminium halohydrates and zirconium chlorohydrates together with amino acids such as glycine, which are disclosed in U.S. Pat. No. 3,792,068 (Luedders et al). Certain of those Al/Zr complexes are commonly called ZAG in the literature. ZAG actives generally contain aluminium, zirconium and chloride with an Al/Zr ratio in a range from 2 to 10, especially 2 to 6, an Al/Cl ratio from 2.1 to 0.9 and a variable amount of glycine. Actives of this preferred type are available from Westwood, from Summit and from Reheis.

Other actives which may be utilised include astringent titanium salts, for example those described in GB 2299506A.

The antiperspirant active will be dissolved in the disperse phase. In this case, the antiperspirant active will often provide from 3 to 60% by weight of the aqueous disperse phase, particularly from 10% or 20% up to 55% or 60% of that phase. The weight of antiperspirant active does not include any water of hydration which may be present in the solid active before it is dissolved.

Optional Ingredients

Optional ingredients in compositions of this invention can include deodorants, for example at a concentration of up to about 10% w/w. Suitable deodorant actives can comprise deodorant effective concentrations of antiperspirant metal salts, deoperfumes, and/or microbicides, including particularly bactericides, such as chlorinated aromatics, including biguanide derivatives, of which materials known as Irgasan DP300™, (Triclosan), Tricloban™, and Chlorhexidine warrant specific mention. A yet another class comprises biguanide salts such as available under the trade mark Cosmosil™.

Other optional ingredients include wash-off agents, often present in an amount of up to 10% w/w to assist in the removal of the formulation from skin or clothing. Such wash-off agents are typically nonionic surfactants such as esters or ethers containing a $C_8$ to $C_{22}$ alkyl moiety and a hydrophilic moiety which can comprise a polyoxyalkylene group (POE or POP) and/or a polyol.

A further optional constituent of the formulation comprises one or more secondary structurants which can be employed in addition to the esterified saccharide which is the primary structurant. The amount of such secondary structurants in the formulation is often zero, and usually not more than 15% of the formulation. It is normally not greater than the amount of the primary structurant.

The secondary structurants employable herein can be non-polymeric or polymeric. Solid linear fatty alcohol and/or a wax may be included but are not preferred. Non-polymeric secondary structurants, perhaps gelling agents of lower gel formation enthalpy, can be included. Gellants can comprise dibenzylidene alditols, e.g. dibenzylidene sorbitol. Further suitable gellants can comprise lanosterol, selected N-acyl amino acid derivatives, including ester and amide derivatives, such as N-lauroyl glutamic acid dibutylamide, which gellants can be contemplated in conjunction with 12-hydroxy stearic acid or an ester or amide derivative thereof. Still further gellants include amide derivatives of di or tribasic carboxylic acids, such as alkyl N,N'dialkylsuccinamides, e.g. dodecyl N,N'-dibutylsuccinamide.

Polymeric structurants which can be employed can comprise organo polysiloxane elastomers such as reaction products of a vinyl terminated polysiloxane and a cross linking agent or alkyl or alkyl polyoxyalkylene-terminated poly (methyl substituted) or poly (phenyl substituted) siloxanes. A number of polyamides have also been disclosed as structurants for hydrophobic liquids. Polymers containing both siloxane and hydrogen bonding groups, which might be used as secondary structurants, have been disclosed in WO 97/36572 and WO 99/06473. If an aqueous disperse phase is present, Polyacrylamides, polyacrylates or polyalkylene oxides may be used to structure or thicken this aqueous phase.

The compositions herein can incorporate one or more cosmetic adjuncts conventionally contemplatable for antiperspirant solids or soft solids. Such cosmetic adjuncts can include skin feel improvers, such as talc or finely divided polyethylene, for example in an amount of up to about 10%; skin benefit agents such as allantoin or lipids, for example in an amount of up to 5%; colours; skin cooling agents other than the already mentioned alcohols, such a menthol and menthol derivatives, often in an amount of up to 2%, all of these percentages being by weight of the composition. A commonly employed adjunct is a perfume, which is normally present at a concentration of from 0 to 4% and in many formulations from 0.25 to 2% by weight of the composition.

Translucent/Transparent Compositions

It is possible to construct the formulation of an emulsion such that the emulsion is translucent or transparent. In order to do this the refractive indices of the water-immiscible continuous phase and the polar or aqueous disperse phase must be matched to each other and the value of refractive index at which they are matched must also approximately match the refractive index of the structurant.

The refractive index of a fibrous network of a structurant can be determined by using that structurant to gel a number of oils or oil mixtures of differing refractive index. When the resulting gel is transparent, the refractive index of the oil or oil mixture(which can be determined by conventional measurement) is a good approximation to the refractive index of the structurant. The oils or mixtures or oils should be chosen from these which are gelled well by the structurant to avoid interfering effects. When the gel is not transparent, but is translucent, it will indicate a refractive index which is not precisely matched to the refractive index of the structurant, and thus indicate an amount of mismatch which can be tolerated without loss of translucency. It is likely that the matched refractive indices of the liquid phases will be not over 0.07 units below and not over 0.04 units above the refractive index of the structurant.

Using this method we have determined the refractive index of a preferred structurant, namely cellobiose octanonanoate, to fall in a range between 1.45 and 1.50, being approximately 1.48 at 22° C. With this structurant we have found that the value at which the refractive indices of the continuous and disperse phases are matched can be somewhat below the refractive index of the structurant, down to a value of 1.42 or even down as far as 1.41 or 1.40. A value slightly above 1.48 would be useable also, but is inconvenient to achieve.

For the continuous phase, silicon-free water-immiscible liquid oils generally have refractive indices in a range from 1.43 to 1.49 at 22° C. and can be used alone or mixed together to give a silicon-free carrier liquid with refractive index in this range. Volatile silicone oils generally have a refractive index slightly below 1.40 at 22° C., but carrier liquid mixtures with refractive indices in the range from 1.41 to 1.46 can be obtained by mixing volatile silicone with other oils. Non-volatile silicone oils generally have refractive indices in a range from 1.45 to 1.48 at 22° C. and so can be included when desired.

The RI of the continuous phase will be very close to the RI of the carrier liquid (usually a carrier liquid mixture) which is its principal component.

For the disperse phase, a solution of an antiperspirant active salt in water alone will generally display a refractive index below 1.425. The refractive index can be raised by incorporating a diol or polyol into the aqueous solution. It is believed to be novel to match the refractive index of a polar disperse phase to that of a structurant network within a continuous phase. Moreover, it can be achieved without using so much diol or polyol as will make the composition excessively sticky.

For the regular production of compositions with optimum transparency it may prove desirable to monitor the refractive indices of the raw materials to detect any batch to batch variation. If necessary the composition of a liquid phase can be adjusted by variation of the quantity of a constituent material.

Mechanical Properties and Product Packages

The compositions of this invention are structured liquids and may be firm or soft in appearance. Even a soft solid has an ability to sustain its own shape, for instance if it is removed from a mould without being subjected to shear it will retain its shape for at least 30 seconds, usually longer.

A composition of this invention will usually be marketed as a product comprising a container with a quantity of the composition therein, where the container has at least one aperture for the delivery of composition, and means for urging the composition in the container towards the delivery aperture. Conventional containers take the form of a barrel of oval cross section with the delivery aperture(s) at one end of the barrel.

A composition of this invention may be sufficiently rigid that it is not apparently deformable by hand pressure and is suitable for use as a stick product in which a quantity of the composition in the form of a stick is accommodated within a container barrel having an open end at which an end portion of the stick of composition is exposed for use. The opposite end of the barrel is closed.

Generally the container will include a cap for its open end and a component part which is sometimes referred to as an elevator or piston fitting within the barrel and capable of relative axial movement along it. The stick of composition is accommodated in the barrel between the piston and the open end of the barrel. The piston is used to urge the stick of composition along the barrel. The piston and stick of composition may be moved axially along the barrel by manual pressure on the underside of the piston using a finger or rod inserted within the barrel. Another possibility is that a rod attached to the piston projects through a slot or slots in the barrel and is used to move the piston and stick. Preferably the container also includes a transport mechanism for moving the piston comprising a threaded rod which extends axially into the stick through a correspondingly threaded aperture in the piston, and means mounted on the barrel for rotating the rod. Conveniently the rod is rotated by means of a handwheel mounted on the barrel at its closed end, i.e. the opposite end to the delivery opening.

If a composition of this invention is softer, but still capable of sustaining its own shape it will be more suited for dispensing from a barrel with a closure instead of an open end, where the closure has one or more apertures through which composition from the barrel can be extruded. The number and design of such apertures is at the discretion of the designer of the package.

The component parts of such containers are often made from thermoplastic materials, for example polypropylene or polyethylene. Descriptions of suitable containers, some of which include further features, are found in U.S. Pat. Nos. 4,865,231, 5,000,356 and 5,573,341.

Measurement of Properties i) Penetrometer

The hardness and rigidity of a composition which is a firm solid can be determined by penetrometry. If the composition is a softer solid, this will be observed as a substantial lack of any resistance to the penetrometer probe.

A suitable procedure is to utilises a lab plant PNT penetrometer equipped with a Seta wax needle (weight 2.5 grams) which has a cone angle at the point of the needle specified to be 9°10'±15'. A sample of the composition with a flat upper surface is used. The needle is lowered onto the surface of the composition and then a penetration hardness measurement is conducted by allowing the needle with its holder to drop under a total weight, (i.e. the combined weight of needle and holder) of 50 grams for a period of five seconds after which the depth of penetration is noted.

Desirably the test is carried out at a number of points on each sample and the results are averaged. Utilising a test of this nature, an appropriate hardness for use in an open-ended dispensing container is a penetration of less than 30 mm in this test, for example in a range from 2 to 30 mm. Preferably the penetration is in a range from 5 mm to 20 mm.

In a specific protocol for this test measurements on a stick were performed in the stick barrel. The stick was wound up to project from the open end of the barrel, and then cut off to leave a flat, uniform surface. The needle was carefully lowered to the stick surface, and then a penetration hardness measurement was conducted. This process was carried out at six different points on the stick surface. The hardness reading quoted is the average value of the 6 measurements.

ii) Texture Analyser

The hardness of a softer solid can be measured by using a texture analyser. This test apparatus can move a blunt probe into or out from a sample at a controlled speed and at the same time measure the applied force. The parameter which is determined as hardness is a function of the peak force and the projected area of indentation.

A specific test protocol used a Stable Micro systems TA.XT2i Texture Analyser. A metal sphere, of diameter 9.5 mm, was attached to the underside of the Texture Analyser's 5 kg load cell such that it could be used for indenting a sample placed beneath it on the base plate of the instrument. After positioning the sample, the sphere position was adjusted until it was just above the sample surface. Texture Expert Exceed software was used to generate the subsequent motion profile used in the test method. This profile initially indented the sphere into the sample at an indentation speed of 0.05 mm/s until a designated force was reached, which was chosen such that the distance of penetration into the sample was less than the radius of the sphere. At this load the direction of motion of the sphere was immediately reversed to withdraw the sphere from the sample at the same speed of 0.05 mm/s. During the course of the test, the data acquired were time(s), distance (mm) and force (N) and the data acquisition rate was 25 Hz.

Suitable samples for measurement were either contained in stick barrels, which had a screw mechanism, or in 15 ml glass jars. For the barrel samples, the stick was wound up until it protruded above the edges of the barrel and then a knife was used to skim the top of the barrel in such a way as to leave a flat uniform surface. The stick was then pushed back into the barrel as far as possible to minimise any mechanical interference resulting from the compliance of the screw mechanism in the pack. Two indents were generally made either side of the screw. The samples in the 15 ml jars needed no surface preparation but only had enough surface area for a single indentation test to be performed.

The data associated with each test were manipulated using standard spreadsheet software and used to calculate the hardness, H, using the following equation:

$$H[N/mm^2] = \frac{F_{max}[N]}{A_p[mm^2]}$$

where $F_{max}$ is the peak load and $A_p$ is the projected area of the indentation remaining on unloading. This area can be calculated geometrically from the plastic indentation depth. This is slightly less than the total penetration depth measured under load because of elastic deformation of the sample. The plastic indentation depth is calculated from a graph of the unloading-force-versus-total-penetration-depth. The initial slope of this unloading data depends on the initial elastic recovery of the sample. The plastic indentation depth is estimated from an intercept between the zero force axis and a straight line drawn at a tangent to the initial part of the unloading slope.

Similar hardness measurements were also done using a desktop Instron Universal Testing Machine (Model 5566) fitted with a 10 N load cell, and the data analysis performed in the same way.

iii) Deposition and Whiteness of Deposit

Another test of the properties of a composition is the amount of the composition which is delivered onto a surface when the composition is drawn across that surface (representing the application of a stick product to human skin). To carry out this test of deposition, a sample of the composition with standardised shape and size is fitted to apparatus which draws the sample across a test surface under standardised conditions. The amount transferred to the surface is determined as an increase in the weight of the substrate to which it is applied. If desired the colour, opacity or clarity of the deposit may subsequently be determined.

A specific procedure for such tests used apparatus to apply a deposit from a stick onto a substrate under standardised conditions and then measures the mean level of white deposits using image analysis.

The substrates used were a: 12×28 cm strip of grey abrasive paper (3M™ P800 WetorDry™ Carborundum paper)

b: 12×28 cm strip of black Worsted wool fabric.

The substrates were weighed before use. The sticks were previously unused and with domed top surface unaltered.

The apparatus comprised a flat base to which a flat substrate was attached by a clip at each end. A pillar having a mounting to receive a standard size stick barrel was mounted on an arm that was moveable horizontally across the substrate by means of a pneumatic piston.

Each stick was kept at ambient laboratory temperature overnight before the measurement was made. The stick was advanced to project a measured amount from the barrel. The barrel was then placed in the apparatus and a spring was positioned to biassed the stick against the substrate with a standardised force. The apparatus was operated to pass the stick laterally across the substrate eight times. The substrate was carefully removed from the rig and reweighed.

Whiteness of Deposit

The deposits from the previous test were assessed for their whiteness after an interval of 24 hours approximately.

This was done using a Sony XC77 monochrome video camera with a Cosmicar 16 mm focal length lens positioned vertically above a black table illuminated from a high angle using fluorescent tubes to remove shadowing. The apparatus was initially calibrated using a reference grey card, after the fluorescent tubes had been turned on for long enough to give a steady light output. A cloth or Carborundum paper with a deposit thereon from the previous test was placed on the table and the camera was used to capture an image. An area of the image of the deposit was selected and analysed using a Kontron IBAS image analyser. This notionally divided the image into a large array of pixels and measured the grey level of each pixel on a scale of 0 (black) to 255 (white). The average of the grey intensity was calculated. This was a measure of the whiteness of the deposit, with higher numbers indicating a whiter deposit. It was assumed that low numbers show a clear deposit allowing the substrate colour to be seen.

It has been found desirable to carry out deposition of a standard stick composition, and determine the whiteness of the deposit, as a control.

iv) Light Transmission

The translucency of a composition may be measured by placing a sample of standardised thickness in the light path of a spectrophotometer and measuring transmittance, as a percentage of light transmitted in the absence of the gel.

We have carried out this test using a dual-beam spectrophotometer. The sample of composition was poured hot into a 4.5 ml cuvette made of polymethylmethacrylate (PMMA) and allowed to cool to an ambient temperature of 20–25° C. Such a cuvette gives a 1 cm thickness of composition. Measurement was carried out at 580 nm, with an identical but empty cuvette in the reference beam of the spectrophotometer, after the sample in the cuvette had been held for 24 hours. We have observed that a composition which gives a transmittance of as little as 1% in this test is perceived by eye as "translucent". If a stick is made from a composition with 3% transmittance, it is possible to see cavities made by boring beneath the surface of the sample. By contrast, a conventional stick structure with stearyl alcohol is so opaque that it is impossible to see beneath its surface. A transmittance measured at any temperature in the range from 20–25° C. is usually adequately accurate, but measurement is made at 22° C. if more precision is required. In a number of preferred examples we have achieved a transmittance of 20% or above.

Preparation

Compositions of this invention can be produced by conventional processes for making suspension or emulsion solids or soft-solids. Such processes involve forming a heated mixture of the composition at a temperature which is sufficiently elevated that all the esterified saccharide structurant dissolves, pouring that mixture into a mould, which may take the form of a dispensing container, and then cooling the mixture whereupon the structurant solidifies into a network of interconnected fibres extending through the water-immiscible liquid phase.

In a suitable procedure for making emulsion formulations, a solution of the esterified structurant in the water-immiscible liquid phase is prepared at an elevated temperature just as for suspension sticks. If any emulsifier is being used, this is conveniently mixed into this liquid phase. Separately an aqueous or hydrophilic disperse phase is prepared by introduction of antiperspirant active into the liquid part of that phase (if this is necessary; antiperspirant actives can sometime be supplied in aqueous solution which can be utilised as is). This solution of antiperspirant active which will become the disperse phase is preferably heated to a temperature similar to that of the continuous phase with structurant therein, but without exceeding the boiling point of the solution, and then mixed with the continuous phase. Alternatively, the solution is introduced at a rate which maintains the temperature of the mixture. If necessary a pressurised apparatus could be used to allow a higher temperature to be reached, but with the structurant materials of this invention this is usually unnecessary. After the two phases are mixed, the resulting mixture is filled into dispensing containers, typically at a temperature 5 to 30° C. above the setting temperature of the composition, and allowed to cool.

Cooling may be brought about by nothing more than allowing the container and contents to cool. Cooling may be assisted by blowing ambient or even refrigerated air over the containers and their contents.

EXAMPLES

The examples below were prepared using a number of materials set out with their proprietary names in the following list. All temperature are in degrees Celsius. Refractive indices were measured at 25° C.

1) octamethyl cyclotetrasiloxane (Volatile cyclic silicone also known as a cyclomethicone; DC 245 from Dow Corning)
2) decamethyl cyclopentasiloxane (Volatile cyclic silicone also known as a cyclomethicone; DC 345 from Dow Corning)
3 & 4) Non-volatile silicone fluids DC 556 and DC 710 (Dow Corning)
5) Polydecene (Silkflo 364NF from Albemarle)
6) Isostearyl Alcohol (abbreviated to ISA—Prisorine 3515 from Unichema)
7) C12–15 alkyl benzoate (Finsolv TN from Fintex)
8) Mineral Oil (Sirius M70 from Dalton)
9) Polypropyleneglycol 14 butylether (Fluid AP from Amercol)
10) Isopropyl myristate (abbreviated to IPM from Unichema)
11) Isohexadecane (Permethyl 101A from Presperse Inc)
12) Isoeicosane (Permethyl 102A from Presperse Inc).
13) Cetyl dimethicone copolyol (Abil EM90 emulsifier from Th. Goldschmidt)
14) C20–C40 alcohols (Unilin 425 from Petrolite)
15) 50% aqueous solution of Al/Zr pentachlorohydrate (Zirkonal 50 from Giulini)
16) Al/Zr Tetrachlorohydrex glycine complex 30% in propylene glycol (WA2Z 8106 from Westwood)
17) Al/Zr tetrachlorohydrex glycine complex (AZG 375 from Summit)
18) Glycerol (from Aldrich)
19) Propylene glycol (from Fisons)
20) N-lauryl-L-glutamic acid di-n-butylamide (GP-1 from Ajinomoto)
21) Bis-phenylpropyldimethicone, a non-volatile silicone fluid (SF 1555 from G E Silicones)
22) Polyglyceryl polyricinolate (Quest PGPR)
23) 1-octyldodecanol (Eutanol G from Henkel/Cognis)
24) Hydrogenated polyisobutene (Panalene-L-14E from Amoco)
25) Hydrogenated polyisobutene (Fancol 800 from Fanning Corporation)
26) Polyglyceryl-3-diisostearate (Lameform TGI from Henkel/Cognis)
27) Polyglyceryl-2-dipolyhydroxystearate (Dehymuls PGPH from Henkel/Cognis)
28) Polyalpha Olefins (Puresyn 4 from Mobil Chemical)
29) Ceteareth 20 (Eumulgin B2 from Henkel)

Example 1

The enthalpy of gelation was measured for a number of structuring agents in three liquids. In each case the gels are made to contain 7 to 7.5 wt % of the structurant in the liquid.

A sample gel, weighing between 18 and 22 mg was placed in a stainless steel calorimeter capsule, which was sealed with an elastomeric O-ring. The capsule was placed in the DSC at room temperature and heated at 10 K/minute to 150° C., held at 150° C. for 60 seconds and cooled at 2 K/minute to −50° C.

The procedure was repeated with DC 345 alone. The data recorded for DC 345 was subtracted from the data for the gel, so that the gel formation appears a departure from a flat baseline. The gelation enthalpy was calculated as the area between the peak and the baseline.

Values of enthalpy (in kJ/mole) were obtained as set out in the following table

| Structurant | DC 345 | Liquid DC 345:ISA (80:20 ratio by weight) | Isostearyl alcohol (ISA) |
|---|---|---|---|
| α-cellobiose octa-octadecanoate | | 360 | |
| α-cellobiose octa-dodecanoate | | 108 | |
| α-cellobiose octa-undecanoate | | 117 | |
| α-cellobiose octa-decanoate | 84.7 | 94.6 | |
| α-cellobiose octa-nonanoate | 65 | 58 | 77 |
| α-cellobiose octa-octanoate | | 57.8 | |
| 12-hydroxystearic acid | | 40 | |
| β-sitosterol and Oryzanol in 1:1 mole ratio | | 22 | |
| N-lauroyl glutamic acid di-n-butylamide (GP-1) | | 11 | 25 |
| lanosterol | 27 | 7 | |

Example 2
(Comparative)

Gels were prepared with lanosterol by a standard procedure in which the ingredients of the gel were placed in a 30 ml glass bottle together with a magnetic stirrer bar. The mixture was stirred and heated until all the lanosterol had dissolved. The bottle was then removed from the heat, the stirrer bar taken out and the contents of the jar left to cool to room temperature.

The following was observed: Lanosterol was found to dissolve at 10.0 wt % in Finsolv TN at 83° C. After cooling to room temperature for 1 hours a hard, transparent gel was obtained. However the gel was found to be unstable at room temperature: large crystalline lumps appeared within hours and spread throughout the entire gel leading to is collapse.

Lanosterol was found to dissolve at 5.0 wt % in 80:20 (wt %) DC 345: Finsolv TN at 85° C. After cooling to room temperature for 1 hour a hard, translucent gel was obtained. However the gel was found to be unstable at room temperature: large crystalline lumps developed after 1 week.

Example 3
(Comparative)

Unsuccessful attempts were made to prepare compositions as set out in the table below, using N-lauroyl glutamic acid di-n-butylamide (GP-1) as structurant The two compositions would have been emulsions where the disperse phase would be a solution of antiperspirant active in water (Zirkonal 50 is a 50% aqueous solution of antiperspirant active).

| Example no | 3a Emulsion | 3b Emulsion |
|---|---|---|
| Continuous phase | | |
| GP-1 (20) | 3.5% | 5% |
| DC 345 (2) | 39% | 43% |
| Isostearyl alcohol (6) | | 11% |
| Finsolv TN (7) | 16.5% | |
| Abil EM90 (13) | 1% | 1% |
| Disperse Phase | | |
| Zirkonal 50 (15) | 40% | 40% |
| Continuous Phase Data | | |
| Temp at which all the GP-1 had dissolved | 122° C. | 119° C. |
| Temperature at which the continuous phase gelled | 116° C. | 99° C. |

In each case the components of the continuous phase were placed in a beaker and the mixture heated with stirring on a hot plate until all the GP-1 structurant dissolved. The temperature at which it dissolved is shown in the table above.

The intention was then to cool the mixture, while still stirring gently to about 85–90° C. in order to add the components of the disperse solid or liquid phase. In all cases the continuous phase gelled at a temperature (shown in the table) above or very close to 100° C., which was too high for safe addition of the disperse phase in an open laboratory.

Safe preparation at this high temperature would have required special measures such as pressurised apparatus.

Example 4

Cellobiose was esterified with nonanoic acid to yield the fully esterified product in the form of its α-anomer following a procedure generally as described in Takada et al, Liquid Crystals, Volume 19, page 441 (1995).

The following materials were used:
β-D-cellobiose, 20 grams, 0.058 moles
Nonanoic acid, 591.6 grams, 3.74 moles
Trifluoroacetic anhydride, 297.6 grams, 1.42 moles.

These materials were obtained from Acros Organics-Fisher Scientific.

Into a 2 liter flange pot equipped with an overhead stirrer, water condenser and addition inlet was placed the nonanoic acid together with the trifluoroacetic anhydride. The resultant clear mixture was stirred up and heated to 100° C. using a silicone oil bath and temperature probe. During heating it was noted that the colour of the reaction mixture darkened and developed a dark brown tinge. After allowing the mixture to stir for one hour at 100° C., the cellobiose was slowly added via a solid powder funnel to the dark activated solution, and a dirty brown suspension was formed which re-dissolved forming a clear black solution within 10–20 minutes.

The reaction flask was then maintained at 100° C. for a total of 6 hours then cooled down to ambient laboratory temperature. Next the contents of the flask were transferred into 2 liters of methanol containing 10% de-ionised water in an ice-cooled 5 liter beaker. Immediately an off-white solid precipitate came out of solution, this was filtered off and collected. The crude solid was recrystallised a total of 4 times from a tetrahydrofuran/methanol solution producing a white solid product.

The product was obtained in a quantity of 31.5 g which was a 37% yield. It had a melting point of 110° C. The infra-red spectrum showed an absorption peak at 1739 $cm^{-1}$ for the ester carbonyl group. The amount of free acid could be determined from its absorption peak at 1705 $cm^{-1}$.

The n.m.r. spectrum showed the amount of cellobiose which was fully esterified to be 93.5% and showed the proportions of product which were the α- and β-anomers, (93.5% α-anomer).

Other esters of cellobiose were prepared in the same way. Samples of esterified cellobiose prepared as above were used to gel various water-immiscible liquids and mixtures of liquids. The procedure was as follows:

0.5 grams esterified cellobiose and 9.5 grams of the liquid (or other proportions to give a total of 10 grams) were weighed directly into a 15 gram or 30 gram glass jar. A small magnetic follower was placed in the jar which was then placed on a hot plate. It was stirred and heated until all of the esterified cellobiose had dissolved in the liquid. This "dissolution temperature" was noted. The jar was then removed from the hot plate, the stirrer was removed from the hot liquid in the jar. A thermometer was placed in the liquid and the contents of the jar were then left undisturbed to cool. The gelling temperature, i.e. the temperature at which the contents gelled, was noted. The jar was left to stand for 24 hours and then the contents of the jar were inspected visually, pressed with a probe and classified qualitatively according to their appearance as a soft, medium or hard gel. The clarity or otherwise of the gel was noted. In most instances the gel was remelted, the remelting temperature was noted, and some of the melt was poured into a plastic (polymethylmethacrylate) cuvette and allowed to cool back to ambient laboratory temperature so that the gel reformed in the cuvette. The transmittance of light through the 1 cm thickness of gel in the cuvette was determined at a wave length of 580 nm using an ultraviolet/visible spectrophotometer.

The following tables show the water-immiscible liquids which were used, the percentage of esterified cellobiose structurant used to gel the liquid, the dissolution temperature, the gelling temperature, the visual appearance of the gel, the remelt temperature and the percentage light transmittance (denoted as %T) through 1 cm of the gel at 580 nm.

| Gelling with α-cellobiose octa-octanoate("CB8" R = $COC_7H_{15}$) | | | | | | |
|---|---|---|---|---|---|---|
| Liquid | % CB8 | Diss Temp | Gel Temp | Remelt Temp | % T | Visual appearance of gel |
| ISA (6) | 5 | 41 | 30 | 41 | | Hard & transparent -> crystal growth |
| | 10 | 41 | 35 | | | Hard & translucent -> crystal growth |
| DC 345 (2) | 5 | 48 | 41 | 50 | 17 | Hard & transparent/ translucent |
| | 10 | 53 | 50 | | | Hard & opaque |
| DC 556 (3) | 5 | 48 | 30 | 45 | 49 | Hard & transparent |
| | 10 | 49 | 35 | | | Hard & transparent |
| Silkflo 364 NF (5) | 5 | 53 | 45 | 51 | 22 | Hard & transparent |
| | 10 | 55 | 50 | | | Hard & opaque |

| Gelling with α-cellobiose octa-nonanoate ("CB9") | | | | | | |
|---|---|---|---|---|---|---|
| Liquid | % CB9 | Diss Temp | Gel Temp | Remelt Temp | % T | Visual appearance of gel |
| ISA (6) | 5 | 57 | 25 | 46 | 78 | Medium/hard & transparent |
| DC 345 (2) | 5 | 62 | 42 | 60 | 15 | Hard & transparent/ translucent |
| DC 566 (3) | 5 | 69 | 29 | 52 | 81 | Hard & transparent |
| Silkflo 364NF (5) | 5 | 71 | 40 | 55 | 78 | Hard & transparent |
| Fluid AP (9) | 5 | 82 | 38 | 55 | 37 | Soft/medium & transparent |
| DC 345:Fluid AP 80:20 wt ratio | 5 | 68 | 28 | 54 | 39 | Soft/medium & transparent |
| DC 710 (4) | 5 | 82 | 48 | 62 | 11 | Medium & translucent |
| DC 710:DC 345 60:40 wt ratio | 5 | 74 | 33 | 60 | 4 | Hard & translucent |

| Gelling with α-cellobiose octa-decanoate ("CB10" R = $COC_9H_{19}$) | | | | | | |
|---|---|---|---|---|---|---|
| Liquid | % CB10 | Diss Temp | Gel Temp | Remelt Temp | % T | Visual appearance of gel |
| Finsolv TN (7) | 5 | 72 | 25 | 38 | | Very soft & transparent gel |
| ISA (6) | 5 | 72 | 25 | 47 | 46 | Medium & transparent |
| | 7 | 68 | 25 | 52 | | Hard & translucent |
| | 10 | 76 | 30 | | | Medium & transparent |
| DC 345 (2) | 5 | 85 | 62 | 71 | 0.02 | Hard & translucent/ opaque |
| | 7 | 84 | 65 | 59 | | Hard & opaque |

-continued

| | | | | | | |
|---|---|---|---|---|---|---|
| DC 556 (3) | 3 | 79 | 46 | 59 | | Medium & transparent |
| | 5 | n/d | 50 | 52 | 2 | Medium/hard & translucent |
| | 7 | 74 | 40 | 67 | | Hard & translucent |
| Fluid AP (9) | 3 | 85 | 35 | 60 | | Medium & transparent |
| | 5 | 82 | 33 | 51 | | Medium & transparent |
| | 7 | 78 | 51 | 53 | 3 | Medium & translucent |
| | 10 | 84 | 45 | | | Medium & translucent/opaque |
| DC 345:Fluid AP 80:20 wt ratio | 5 | 73 | 25 | 55 | <0.01 | Medium & translucent/opaque |
| | 7 | 82 | 36 | 49 | | Hard & opaque |
| | 10 | 83 | 41 | | | Hard & opaque |
| DC 710 (4) | 5 | 100 | 80 | 80 | 0.15 | Medium & opaque |
| DC 710:DC 345 60:40 wt ratio | 5 | 92 | 65 | 65 | 1 | Medium & translucent/opaque trans |

Gelling with α-cellobiose octa-dodecanoate ("CB12" R = COC$_{11}$H$_{23}$)

| Liquid | % CB12 | Diss Temp | Gel Temp | Remelt Temp | % T | Visual appearance of gel |
|---|---|---|---|---|---|---|
| ISA (6) | 5 | 54 | 30 | 48 | 12 | Soft & transparent/translucent |
| DC 345 (2) | 5 | 50 | 48 | 50 | 0.17 | Soft & opaque |
| DC 556 (3) | 5 | 60 | 35 | 48 | 17 | Medium & transparent/translucent |
| Silkflo 364 NF (5) | 5 | 53 | 45 | 55 | 3 | Medium & transparent |
| Fluid AP (9) | 5 | 63 | 43 | 55 | 4 | Soft & transparent/translucent |
| DC 345:Finsolv TN 80:20 wt ratio | 5 | 65 | 29 | 42 | 3 | soft & translucent |
| DC 345:Fluid AP 80:20 wt ratio | 5 | 63 | 42 | 50 | 0.25 | Soft/medium & opaque |
| DC 710 (4) | 5 | 65 | 57 | 65 | 1 | Medium & opaque |
| DC 710:DC 345 60:40 wt ratio | 5 | 65 | 48 | 55 | 39 | Soft & transparent |

Gelling with α-cellobiose octa-octadecanoate ("CB18" R = COC$_{17}$H$_{35}$)

| Liquid | % CB18 | Diss Temp | Gel Temp | Remelt Temp | % T | Visual appearance of gel |
|---|---|---|---|---|---|---|
| Finsolv TN (7) | 5 | 68 | 47 | 60 | 0.12 | very soft & opaque |
| | 7 | 68 | 47 | | | |
| IPM (10) | 5 | 68 | 50 | 59 | 0.01 | very soft & opaque |
| | 7 | 72 | 50 | | | very soft & opaque |
| ISA (6) | 5 | 68 | 58 | 62 | 0.03 | very soft & opaque |
| | 7 | 70 | 61 | | | soft & opaque |
| DC 345 (2) | 5 | 85 | 82 | 80 | <0.01 | soft & opaque |
| | 7 | 87 | 86 | | | soft & opaque |
| | 10 | 85 | 84 | | | medium & opaque |
| DC 556 (3) | 5 | 77 | 76 | 75 | 0.08 | soft & opaque |
| | 7 | 83 | 79 | | | soft & opaque |
| | 10 | 83 | 79 | | | medium & opaque |
| Silkflo 364 NF (5) | 5 | 72 | 66 | 75 | 0.11 | medium & opaque |
| | 7 | 72 | 68 | | | medium & opaque |
| | 10 | 79 | 69 | | | medium & opaque |
| Fluid AP (9) | 5 | 78 | 76 | 78 | 0.01 | soft & opaque |
| | 7 | 82 | 77 | | | medium & opaque |
| | 10 | 82 | 81 | | | soft & opaque |

It can be seen from the above table that the gelation temperatures were low. The remelt temperatures were generally below 80° C. and most of the compositions could be prepared without any need to exceed 85° C.

Example 5

Opaque emulsion sticks were prepared with formulations as set out in the table below.

To prepare these sticks, the cyclomethicone was mixed with the other organic liquids (if any) including the cetyl dimethicone copolyol which functioned as an emulsifier (silicone surfactant) and the mixture was heated with gentle stirring to a temperature 5 to 10° C. above the temperature at which the structurant had been found to dissolve in a preliminary test. The esterified cellobiose was then added and allowed to dissolve.

The disperse phase (also referred to as internal phase) was an aluminium zirconium active dissolved in water or in a mixture of a polyol and water. This disperse phase was pre-heated to the same temperature as the organic oils containing the esterified cellobiose and added slowly to them over a period of one minute while mixing with a Silverson mixer. After addition was complete the formulation was mixed at higher speed for five minutes. Stirring speed was then reduced for a further one minute after which the mixture was poured into stick barrels and allowed to cool undisturbed to ambient laboratory temperature. The sticks were tested by penetrometer, by texture analyser and for whiteness of deposits, in each instance by the test procedures given earlier. All of the sticks were opaque although without the chalky white appearance of a commercial white stick (CWS) structured with stearyl alcohol and castor wax whose test results are given at the right of the table.

| Examples | 5.1 | 5.2 | 5.3 | CWS |
|---|---|---|---|---|
| | % by weight | | | |
| Cyclomethicone DC 245 (1) | 18 | 22.25 | 21.7 | |
| Polydecene (5) | 22.75 | 27.5 | 27.4 | |
| PPG-14 Butyl Ether (9) | 4.5 | 5.5 | 5.4 | |
| Cellobiose octa-nonanoate | 3.75 | 3.75 | 4.5 | |
| Cetyl Dimethicone Copolyol (13) | 1 | 1 | 1 | |
| Zirkonal 50 (15) | 40 | 40 | 40 | |
| Water | 10 | — | — | |
| Properties | | | | |
| penetration depth (mm) | 16.8 | 17.5 | 15.7 | 9.8 |
| Hardness by texture analyser (N/mm$^2$) | 0.11 | 0.10 | 0.12 | — |
| Whiteness on grey paper 24 hours after deposition | 19 | 16 | 16 | 118 |
| Whiteness on black wool 24 hours after deposition | 28 | 28.5 | 27 | 186 |

Example 6

Sticks were prepared and tested in accordance with the procedure given in Example 5. The sticks were tested for hardness by texture analyser and/or by penetrometer. They were observed to give deposits of low whiteness, but numerical data were not recorded.

For some sticks in this example the refractive indices of the water-immiscible continuous phase and the polar antiperspirant active solution were matched sufficiently to give translucent sticks. Some values of transmittance are shown.

| Examples | 6.1 | 6.2 | 6.3 | 6.4 | 6.5 |
|---|---|---|---|---|---|
| | % by weight | | | | |
| DC245 (1) | 44 | 21.625 | 21.625 | 21.625 | 18 |
| Silkflo364 (5) | — | — | — | 21.625 | 4 |
| Permethyl 102A (12) | — | 21.625 | — | — | — |
| SF1555 (21) | — | — | 21.625 | — | 22 |
| Abil EM90 (13) | 1 | — | — | — | 1 |
| Quest PGPR (22) | — | 1.75 | 1.75 | 1.75 | — |
| Esterified Cellobiose-C9 | 5 | 5 | 5 | 5 | 5 |
| Zirkonal 50 (15) | 39 | 40 | 40 | 40 | 40 |
| Glycerol (18) | — | 8 | 9 | 8.75 | 10 |
| Water | 11 | 2 | 1 | 1.25 | — |
| Properties | | | | | |
| Penetration depth (mm) | 9.3 | 12 | 11.3 | 13 | |
| Hardness by texture analyser (N/mm$^2$) | 0.10 | 0.12 | 0.12 | 0.21 | 0.13 |

| Examples | 6.6 | 6.7 | 6.8 | 6.9 | 6.10 |
|---|---|---|---|---|---|
| | % by weight | | | | |
| Cyclomethicone DC 245 (1) | 7.6 | 6.8 | 36.5 | 1.7 | 1.25 |
| isostearyl alcohol (6) | — | — | — | 23.3 | — |
| octyldodecanol (23) | — | — | — | — | 23.1 |
| SF1555 (21) | 37.43 | 37.7 | 7 | — | — |
| Silkflo 364 (5) | — | — | — | 16.8 | 17.65 |
| Esterified Cellobiose-C10 | 8.12 | 7.3 | 7.8 | 7 | 7 |
| Cetyl Dimethicone Copolyol (Abil EM90) (13) | 1.1 | 1 | 1 | 1 | 1 |
| Westwood active (16) | 43.54 | 41 | 42 | 40 | 40 |
| Glycerol (18) | — | 4.7 | 5.2 | 6.8 | 6.5 |
| Water | 2.21 | 1.5 | 0.5 | 3.4 | 3.5 |
| Properties | | | | | |
| Matched RI of phases | 1.45 | 1.45 | 1.46 | 1.45 | 1.45 |
| penetration depth (mm) | 9.1 | 6.9 | 8.7 | 8.8 | 9.1 |
| Hardness by texture analyser (N/mm$^2$) | 0.37 | 0.03 | 0.08 | 0.04 | 0.19 |
| Transmittance at 580 nm (%) | 8 | 3 | 5 | 6 | 5 |

| Examples | 6.11 | 6.12 | 6.13 | 6.14 |
|---|---|---|---|---|
| | % by weight | | | |
| DC245 (1) | 12 | 11.32 | — | — |
| Silkflo 364 (5) | 32.5 | 30.68 | 39 | 41.5 |
| Abil EM90 (13) | 0.5 | 0.5 | 1 | 1 |
| Esterified Cellobiose-C10 | 5 | 7.5 | 10 | 7.5 |
| Zirkonal 50 (15) | 33 | 33 | — | — |
| Westwood active (16) | — | — | 48.06 | 48.06 |
| Glycerol (18) | 17 | 17 | — | — |
| water | — | — | 1.94 | 1.94 |
| Properties | | | | |
| penetration depth (mm) | 19 | 14 | 7.3 | 9.6 |
| Hardness by texture analyser (N/mm$^2$) | 0.44 | 0.07 | 0.47 | 0.15 |

Example 7

The procedure of Example 5 was repeated to prepare a number of emulsion sticks with formulations set out in the following tables. The continuous and disperse phases were formulated to have refractive indices which matched closely at the value given in the tables. These sticks were tested as before and the properties are also given in these tables.

| Examples | 7.1 | 7.2 | 7.3 | 7.4 | 7.5 | 7.6 |
|---|---|---|---|---|---|---|
| | % by weight | | | | | |
| Cyclomethicone DC245 (1) | 22.625 | 18.75 | 25.5 | 19 | 26 | 17.75 |
| Mineral Oil (8) | 22.625 | — | — | — | — | — |
| Polydecene (5) | — | 22.5 | 15.75 | 22 | 15 | 22 |
| PPG-14 Butyl Ether (9) | — | 4 | 4 | — | — | 4.25 |
| Isostearyl Alcohol (6) | — | — | — | 4.25 | 4.25 | — |
| Cellobiose octa-nonanoate | 3.75 | 3.75 | 3.75 | 3.75 | 3.75 | 5 |
| Cetyl Dimethicone Copolyol (13) | 1 | 1 | 1 | 1 | 1 | 1 |
| Zirkonal 50 (15) | 40 | 40 | 40 | 40 | 40 | 40 |
| Glycerol (18) | 10 | 10 | 7.5 | 10 | 7.5 | 10 |
| Water | — | — | 2.5 | — | 2.5 | — |
| | Properties | | | | | |
| Matched refractive index of phases | 1.43 | 1.43 | 1.425 | 1.435 | 1.425 | 1.43 |
| penetration depth (mm) | 19.3 | 18.5 | 17.3 | 24.7 | 23.6 | 12.4 |
| Hardness by texture analyser (N/mm$^2$) | 0.11 | 0.12 | 0.08 | 0.07 | 0.06 | 0.17 |
| Whiteness on grey paper 24 hours after deposition | — | 15 | 16 | 18 | 19 | 16 |
| Whiteness on black wool 24 hours after deposition | — | 24 | 28 | 25 | 30 | 26 |
| Transmittance at 580 nm | — | 38% | 33% | 41% | 35% | 51% |

| Examples | 7.7 | 7.8 | 7.9 | 7.10 | 7.11 |
|---|---|---|---|---|---|
| | % by weight | | | | |
| Cyclomethicone DC245 (1) | 16.75 | 18 | 14.02 | 28.4 | 4.5 |
| Polydecene (5) | 20.75 | 22.75 | 17.72 | 13.1 | 50.75 |
| PPG-14 Butyl Ether (9) | 4 | 4.5 | 3.51 | 3.75 | — |
| Cellobiose octa-nonanoate | 7.5 | 3.75 | 3.75 | 3.75 | 3.75 |
| Cetyl Dimethicone Copolyol (13) | 1 | 1 | 1 | 1 | 1 |
| Zirkonal 50 (15) | 40 | — | 40 | 40 | — |
| Glycerol (18) | 10 | 4 | 17.5 | 6.25 | 12 |
| Water | — | 14 | 2.5 | 3.75 | 8 |
| Propylene glycol (19) | — | 12 | — | — | — |
| AZG 375 (17) | — | 20 | — | — | 20 |
| | Properties | | | | |
| Matched RI of phases | 1.43 | 1.43 | 1.43 | 1.42 | 1.45 |
| penetration depth (mm) | 11 | 14.5 | 14.9 | 15.1 | 14.8 |
| Hardness by texture analyser (N/mm$^2$) | 0.29 | 0.11 | 0.14 | 0.13 | 0.11 |
| Whiteness on grey paper 24 hours after deposition | 17 | 20 | 18 | 21 | 16 |
| Whiteness on black wool 24 hours after deposition | 25 | 28 | 25 | 31 | 19 |
| Transmittance at 580 nm | 48% | 82% | 65% | 30% | 72% |

| Examples | 7.12 | 7.13 | 7.14 | 7.15 | 7.16 |
|---|---|---|---|---|---|
| | % by weight | | | | |
| Cyclomethicone DC245 (1) | 41.85 | 35.4 | 10.04 | 10.64 | 6.96 |
| Permethyl 101A (11) | 2.15 | — | — | — | — |
| Permethyl 102A (12) | — | 8.6 | — | — | — |
| Polydecene (5) | — | — | 12.7 | 13.45 | 8.8 |
| PPG-14 Butyl Ether (9) | — | — | 2.51 | 2.66 | 1.74 |
| Cellobiose octa-nonanoate | 5 | 5 | 3.75 | 2.25 | 1.5 |
| Cetyl Dimethicone Copolyol (13) | 1 | 1 | 1 | 1 | 1 |
| Zirkonal 50 (15) | 40 | 40 | 52.71 | 52.71 | 60.24 |
| Glycerol (18) | 0.75 | 4.5 | 17.29 | 17.29 | 19.76 |
| Water | 9.25 | 5.5 | — | — | — |

-continued

|  | Properties | | | |
|---|---|---|---|---|
| Matched refractive index of phases | 1.40 | 1.41 | 1.43 | 1.43 |
| penetration depth (mm) | 13.5 | 13.2 | 12.0 | 16.8 |
| Hardness by texture analyser (N/mm$^2$) | 0.16 | 0.15 | 0.13 | 0.07 |
| Whiteness on grey paper 24 hours after deposition | 59 | 61 | 24 | 24 |
| Whiteness on black wool 24 hours after deposition | 122 | 24 | 14.9 | 16.2 |
| Transmittance at 580 nm | 2.7% | 5% | 33% | 73% |

Example 8

The procedure of Example 5 was repeated to prepare a number of emulsion sticks with formulations set out in the following tables. As in Example 7, the continuous and disperse phases were formulated to have refractive indices which matched closely at the value given in the tables. The sticks were tested for hardness by texture analyser and/or by penetrometer. They were observed to give deposits of low whiteness, consistent with their good clarity, but numerical data were not recorded.

The refractive indices of sample quantities of the water-immiscible liquid mixture and the antiperspirant active solutions were checked before making the sticks. If necessary their formulations were modified very slightly to optimise the refractive index match.

| Examples | 8.1 | 8.2 | 8.3 | 8.4 | 8.5 | 8.6 |
|---|---|---|---|---|---|---|
|  | % by weight | | | | | |
| Permethyl 102A (12) | 41.36 | — | — | — | — | — |
| Panalene L-14E (24) | — | — | 22 | — | — | — |
| Fancol 800 (25) | — | — | — | 22 | 22 | — |
| Puresyn 4 (28) | — | — | — | — | — | 22 |
| DC245 (1) | 2.64 | 11.4 | 22 | 22 | 22 | 22 |
| SF 1555 (21) | — | 34.1 | — | — | — | — |
| Esterified cellobiose C9 | 5 | 4.9 | 5 | 5 | 5 | 5 |
| Abil EM90 (13) | 1 | 1 | 1 | 1 | 1 | 1 |
| Zirkonal 50 (15) | — | — | 40 | 40 | 36.6 | 40 |
| Westwood active (16) | 50 | 48.6 | — | — | — | — |
| Glycerol (18) | — | — | 9.35 | 7.5 | 13.4 | 8.75 |
| Water | — | — | 0.65 | 2.5 | — | 1.25 |
|  | Properties | | | | | |
| Matched RI of phases (at 25° C.) | 1.46 | 1.45 | 1.431 | 1.425 | 1.437 | 1.429 |
| penetration depth (mm) | 9 | 11 | 10.5 | 12.1 | 7.9 | 8.8 |
| Hardness by texture analyser (N/mm$^2$) | 0.11 | 0.11 | 0.13 | 0.12 | 0.11 | 0.10 |
| Transmittance at 580 nm (%) | 68 | 70 | 40 | 6 | 70 | 37 |

| Examples | 8.7 | 8.8 | 8.9 | 8.10 | 8.11 |
|---|---|---|---|---|---|
|  | % by weight | | | | |
| DC245 (1) | 22 | 22.25 | 22.25 | 21.625 | — |
| DC556 (3) | 22 | — | — | — | — |
| Silkflo364 (5) | — | — | — | — | 44 |
| Permethyl 102A (12) | — | 22.25 | — | — | — |
| Panalene-L-14E (24) | — | — | — | 21.625 | — |
| SF1555 (21) | — | — | 22.25 | — | — |
| Abil EM90 (13) | 1 | 0.5 | 0.5 | — | 1 |
| Lameform TGI (26) | — | — | — | 0.875 | — |
| Dehymuls PGPH (27) | — | — | — | 0.875 | — |
| Esterified cellobiose C9 | 5 | 5 | 5 | 5 | 5 |
| Zirkonal 50 (15) | 40 | 40 | 40 | 40 | 50 |
| Glycerol (18) | 9 | 8 | 9 | 9.8 | — |
| Water | 1 | 2 | 1 | 0.2 | — |
|  | Properties | | | | |
| Matched RI of phases (at 25° C.) | 1.428 | 1.43 | 1.43 | 1.43 | 1.46 |

-continued

|  |  |  |  |  |  |
|---|---|---|---|---|---|
| penetration depth (mm) | 9.0 | 11 | 11 | 10.5 | 9 |
| Hardness by texture analyser (N/mm$^2$) | 0.10 | 0.09 | 0.16 | 0.13 | 0.13 |
| Transmittance at 580 nm (%) | 40 | 22 | 33 | 36 | 24 |

| Examples | 8.12 | 8.13 | 8.14 | 8.15 | 8.16 | 8.17 |
|---|---|---|---|---|---|---|
| | % by weight | | | | | |
| DC245 (1) | — | — | — | 22 | 22 | 18 |
| Silkflo364 (5) | 44 | — | — | — | — | 5.3 |
| Permethyl 102A (12) | — | 44 | — | 22 | — | — |
| Panalene-L-14E (24) | — | — | 44 | — | — | — |
| SF1555 (21) | — | — | — | — | 22 | — |
| Octyldodecanol (23) | — | — | — | — | — | 21.9 |
| Abil EM90 (13) | 1 | 1 | 1 | 1 | 1 | 1 |
| Esterified Cellobiose C9 | 5 | 5 | 5 | 5 | 5 | 5 |
| Zirkonal 50 (15) | 18 | 21.5 | 12 | — | — | 37.8 |
| AZG-375 (17) | — | — | — | 25 | 25 | — |
| Glycerol (18) | 32 | 28.5 | 38 | 0.6 | 2.5 | 11 |
| Water | — | — | — | 24.4 | 22.5 | — |
| Properties | | | | | | |
| Matched refractive index of phases (at 25° C.) | 1.45 | 1.45 | 1.46 | 1.43 | 1.43 | 1.43 |
| penetration depth (mm) | 9 | 9 | 7 | 9 | 8 | — |
| Hardness by texture analyser (N/mm$^2$) | 0.13 | 0.15 | 0.20 | — | 0.21 | 0.12 |
| Transmittance at 580 nm (%) | 74 | 46 | 82 | 53 | 41 | 24 |

Example 9

The procedure of Example 5 was used to prepare a number of emulsion sticks with formulations set out in the following table. These sticks did not contain antiperspirant active. They would be useful as moisturizing stick or lip salve and their compositions could be used as the basis for other, probably opaque, cosmetic stick products. The continuous and disperse phases were formulated to have refractive indices which matched closely at the values given in the table, but evaporative losses during processing interfered with this. The sticks were tested for hardness by texture analyser and/or by penetrometer.

| Examples | 9.1 | 9.2 | 9.3 | 9.4 |
|---|---|---|---|---|
| | % by weight | | | |
| DC245 (1) | 22 | 22 | 16.72 | 19.36 |
| Silkflo 364 (5) | 22 | — | 27.28 | — |
| SF1555 (21) | — | 22 | — | 24.64 |
| Abil EM90 (13) | 1 | 1 | 1 | 1 |
| Esterified Cellobiose C9 | 5 | 5 | 5 | 5 |
| Glycerol (18) | 33.5 | 37.5 | — | — |
| Water | 16.5 | 12.5 | — | — |
| Propylene Glycol (19) | — | — | 50 | 50 |
| Properties | | | | |
| Matched RI of phases (at 25° C.) | 1.42 | 1.43 | 1.43 | 1.43 |
| penetration depth (mm) | 9 | 9 | — | 10 |
| Hardness by texture analyser (N/mm$^2$) | 0.13 | 0.15 | 0.15 | — |

Example 10

The procedure of Example 5 was used to prepare translucent emulsion sticks with the formulation below in which the structurant is α-cellobiose octa-undecanoate ("CB11"). As in Example 7, the continuous and disperse phases were formulated to have refractive indices which matched closely at the value given. The sticks were tested for hardness by texture analyser and/or by penetrometer. They were observed to give deposits of low whiteness.

| Ingredients | percent by weight |
|---|---|
| DC245 (1) | 11 |
| Silkflo 364 (5) | 33 |
| Abil EM90 (13) | 1 |
| Esterified Cellobiose C11 | 5 |
| Zirkonal 50 (15) | 33 |
| Glycerol (18) | 17 |
| Properties | |
| Matched RI of phases (at 25° C.) | 1.44 |
| penetration depth (mm) | 16 |
| Hardness by texture analyser (N/mm$^2$) | 0.05 |
| Transmittance at 580 nm (%) | 6 |

Example 11

The procedure of Example 5 was used to prepare an opaque emulsion stick of the following formulation, which included agents to assist wash-off.

| Ingredients | percent by weight |
| --- | --- |
| DC245 (1) | 16.4 |
| Silkflo 364 (5) | 24.6 |
| Abil EM90 (13) | 1 |
| Esterified cellobiose C9 | 5 |
| Zirkonal 50 (15) | 40 |
| Glycerol (18) | 10 |
| Ceteareth 20 (29) | 2.5 |
| $C_{20-40}$ alcohols (14) | 0.5 |

What is claimed is:

1. A cosmetic composition which is a structured emulsion comprising:
    i) a continuous phase containing water-immiscible liquid carrier and a fibre-forming structurant present in the continuous phase, which is effective to gel the composition upon cooling from a temperature at which the structurant is in solution in the carrier liquid, and
    ii) a disperse phase which is a solution of antiperspirant active in water, water-soluble solvent or a mixture of them,
    wherein the structurant has an enthalpy of gelation in the carrier liquid with a magnitude of at least 30 kJ/mole.

2. A cosmetic composition which is a structured emulsion comprising:
    i) a continuous phase containing water-immiscible liquid carrier and a fibre-forming structurant present in the continuous phase, which is effective to gel the composition upon cooling from a temperature at which the structurant is in solution in the carrier liquid, and
    ii) a disperse phase which is a solution of antiperspirant active in water, water-soluble solvent or a mixture of them,
    wherein the structurant is able to gel one or more of
        decamethyl cyclopentasiloxane
        an 80:20 wt % mixture of decamethyl cyclopentasiloxane
            and isostearyl alcohol
        isostearyl alcohol
        with an enthalpy of gelation in at least one of the liquids with a magnitude of at least 30 kJ/mole.

3. A composition according to claim 2 wherein the structurant is able to gel an 80:20 wt % mixture of decamethyl cyclopentasiloxane and isostearyl alcohol with an enthalpy of gelation having a magnitude of at least 30 kJ/mole.

4. A composition according to claim 2 wherein the structurant is able to gel an 80:20 wt % mixture of decamethyl cyclopentasiloxane and isostearyl alcohol with an enthalpy of gelation having a magnitude of at least 45 kJ/mole.

5. A composition according to claim 1 wherein the disperse phase contains a diol or polyol.

6. A composition according to claim 1 which contains from 0.1% to 10% by weight of a nonionic emulsifier.

7. A composition according to claim 1 which does not contain more than 5% by weight of any fatty alcohol which is solid at 20° C.

8. A composition according to claim 1 which does not contain more than 2% by weight of any fatty alcohol which is solid at 20° C.

9. A composition according to claim 1 which does not contain more than 8% by weight of ethanol or any monohydric alcohol with a vapour pressure above 1.3 kPa at 22° C.

10. A composition according to claim 1 wherein the water-immiscible liquid carrier contains a volatile silicone and optionally a non-volatile silicone.

11. A composition according to claim 1 claims wherein the water-immiscible carrier liquid contains silicone oil in an amount which is at least 10% by weight of the composition.

12. A composition according to claim 1 containing from 0.1 to 12% by weight of the structurant.

13. A composition according to claim 1 claims which is an antiperspirant composition comprising an antiperspirant active dissolved in said disperse phase.

14. A composition according to claim 13 wherein the antiperspirant active comprises an aluminium and/or zirconium halohydrate, an activated aluminium and/or zirconium halohydrate, or an aluminium and/or zirconium complex or an activated aluminium and/or zirconium complex.

15. A composition according to claim 14 wherein the antiperspirant active is a halohydrate or complex in which aluminium and zirconium are both present.

16. A composition according to claim 1 wherein the proportion of antiperspirant active is from 5 to 40% by weight of the composition.

17. A composition according to claim 1 in which a firm gel such that a penetrometer needle with a cone angle of 9 degrees 20 minutes, drops into the gel for no more than 30 mm when allowed to drop under a total weight of 50 grams for 5 seconds.

18. A composition according to claim 1 claims which is translucent or transparent.

19. A composition according to claim 1 which has at least 1% light transmittance at 580 nm through a 1 cm thickness of the composition at 22° C.

20. A composition according to claim 1 accommodated within a dispensing container.

21. A cosmetic product comprising a composition according to claim 1 and a dispensing container which accommodates the composition and has at least one aperture for delivery of the contents of the container and means for urging the contents of the container to the said aperture or apertures.

22. A product according to claim 21 wherein the composition is in the form of a stick and the container has an open end at which an end portion of the stick of composition is exposed for use.

23. A process for the production of a composition according to claim 1 comprising, not necessarily in any order, the steps of
    incorporating a structurant into a water-immiscible liquid carrier
    mixing the liquid carrier with a disperse liquid phase,
    heating the liquid carrier or a mixture containing it to an elevated temperature at which the structurant is soluble in the water-immiscible liquid carrier, followed by cooling or permitting the mixture to cool to a temperature at which it is thickened or solidified.

24. A process according to claim 23 which includes a step of pouring the mixture at elevated temperature into a dispensing container and allowing it to cool therein so as to produce a product according to claim 21.

25. A method for preventing or reducing perspiration on human skin comprising topically applying to the skin a composition according to claim 1.

26. A composition according to claim 1 which further comprises a non-silicone hydrophobic organic liquid selected from the group consisting of hydrocarbons, hydrophobic aliphatic esters, aromatic esters, hydrophobic alcohols and hydrophobic ethers.

27. A composition according to claim 1, wherein said composition has at least 3% light transmittance at 580 nm through a 1 cm thickness of said composition at 22° C.

28. A cosmetic composition which is a structured emulsion comprising:
 (i) a continuous phase containing water-immiscible liquid carrier and a fiber forming structurant present in the continuous phase which is effective to gel the composition upon cooling from a temperature at which the structurant is in solution in the carrier liquid; and
 (ii) a disperse phase which is a solution of antiperspirant active in water, water-soluble solvent or a mixture of them,
 wherein the structurant has an enthalpy of gelation in the carrier liquid with a magnitude of at least 45 kJ/mole.

29. A cosmetic composition which is a structured emulsion comprising:
 (i) a continuous phase containing water-immiscible liquid carrier and a fiber-forming structurant present in the continuous phase, which is effective to gel the composition upon cooling from a temperature at which the structurant is in solution in the carrier liquid; and
 (ii) a disperse phase which is a solution of antiperspirant active in water, water-soluble solvent or a mixture of them,
 wherein the structurant is able to gel one or more of:
  decamethylcyclopentasiloxane;
  an 80:20 wt. % mixture of decamethylcyclopentasiloxane and isostearyl alcohol;
  isostearyl alcohol;
  with an enthalpy of gelation in at least one of the liquids with a magnitude of at least 45 kJ/mole.

* * * * *